(12) United States Patent
Schwilch et al.

(10) Patent No.: US 9,606,201 B2
(45) Date of Patent: Mar. 28, 2017

(54) ELECTRICAL CIRCUIT IN THE MAGNETIC FIELD OF AN MR APPARATUS

(71) Applicant: BRUKER BIOSPIN AG, Faellanden (CH)

(72) Inventors: Arthur Schwilch, Uster (CH); Daniel Marek, Schwerzenbach (CH); Martin Luke, Faellanden (CH)

(73) Assignee: Bruker BioSpin AG, Faellanden (CH)

( * ) Notice: Subject to any disclaimer, the term of this patent is extended or adjusted under 35 U.S.C. 154(b) by 646 days.

(21) Appl. No.: 14/072,826

(22) Filed: Nov. 6, 2013

(65) Prior Publication Data
US 2014/0139221 A1  May 22, 2014

(30) Foreign Application Priority Data
Nov. 16, 2012  (DE) .................. 10 2012 220 978

(51) Int. Cl.
  *G01R 33/34* (2006.01)
  *G01R 33/32* (2006.01)
  *A61B 5/055* (2006.01)
  *G01R 33/36* (2006.01)

(52) U.S. Cl.
  CPC ............. *G01R 33/32* (2013.01); *A61B 5/055* (2013.01); *G01R 33/34015* (2013.01); *G01R 33/3621* (2013.01); *G01R 33/3657* (2013.01); *G01R 33/3628* (2013.01)

(58) Field of Classification Search
  CPC .............. G01R 33/34023; G01R 33/31; G01R 33/3403; G01R 33/34015; G01R 33/3621; G01R 33/3657; A61B 5/055
  See application file for complete search history.

(56) References Cited

U.S. PATENT DOCUMENTS

| 4,939,563 A | 7/1990 | Fang et al. |
| 5,247,256 A | 9/1993 | Marek |
| 2008/0061783 A1 | 3/2008 | Schwilch |
| 2010/0231215 A1* | 9/2010 | Ma ............... G01R 33/3403 324/307 |
| 2011/0187369 A1 | 8/2011 | Rivas Davila |
| 2011/0194256 A1 | 8/2011 | De Rijek |

(Continued)

FOREIGN PATENT DOCUMENTS

| EP | 0 782 005 | 7/1997 |
| JP | S6142080 | 2/1986 |

(Continued)

*Primary Examiner* — Clayton E Laballe
*Assistant Examiner* — Ruifeng Pu
(74) *Attorney, Agent, or Firm* — Paul Vincent

(57) ABSTRACT

An electrical circuit with one or more semiconductor components (10) is characterized in that at least one semiconductor junction of at least one of the semiconductor components of the electrical circuit is disposed such that the average direction of motion of the charge carriers in the semiconductor junction is essentially parallel to the lines of force of the magnetic field $B_0$, wherein the corresponding semiconductor component is disposed directly on a substrate (12), which is made of a material with good thermal conduction properties. In this way, undistorted characteristics of the semiconductor component used can be ensured despite the very strong magnetic field and the low operating temperatures.

15 Claims, 6 Drawing Sheets

(56) References Cited

U.S. PATENT DOCUMENTS

2012/0062231 A1\* 3/2012 Saha .................. A61B 5/055
                                                        324/318
2012/0212224 A1    8/2012 Burns

FOREIGN PATENT DOCUMENTS

| JP | 63-197440  | 8/1988  |
|----|------------|---------|
| JP | 63-222755  | 9/1988  |
| JP | 03-084975  | 4/1991  |
| JP | H11201922  | 7/1999  |
| JP | 2001-074043| 3/2001  |
| JP | 2008228765 | 10/2008 |

\* cited by examiner

Prior Art

Prior Art

ELECTRICAL CIRCUIT IN THE MAGNETIC FIELD OF AN MR APPARATUS

This application claims Paris convention priority of DE 10 2012 220 978.6 filed Nov. 16, 2012 the entire disclosure of which is hereby incorporated by reference.

BACKGROUND OF THE INVENTION

The invention concerns an electrical circuit with one or more semiconductor components for use in an apparatus for MR (="magnetic resonance") spectroscopy or tomography with a preferably superconducting magnet coil system for producing a magnetic field in the direction of a z-axis in a working volume disposed on the z-axis about z=0, wherein the electrical circuit is disposed in the MR apparatus as part of a cryogenic MR receiver and/or MR transmitter device at an operating temperature below 100K and in a magnetic field $B_0$ of at least 1T.

Such a configuration is known from Wosik J, Nesteruk K, Kamel M R, Ip F, Xue L, Wright A C, Wehrli F W, Cryogenic Varactor-Tuned 4-element Array and Cryostat for µ-MRI of Trabecular Bone in the Distal Tibia, Proc. Intl. Soc. Mag. Reson. Med. 16 (2008) (=Reference [11]).

In NMR (=Nuclear Magnetic Resonance), especially in MRI (=Magnetic Resonance Imaging), cryogenically cooled receiver systems can be used to enhance the sensitivity for reception of radio-frequency signals. Cooled coil configurations are used for this purpose.

Such a coil configuration for MRI is shown in FIG. 2. A magnet 20 with the magnetic field $B_0$ is located in a Dewar 21. The shim and gradient system 22 and the transmitter and receiver device are located in the room temperature bore 23 of the magnet 20. In the example shown, this consists of a transmitter coil 24 which, in this case, is implemented as a volume coil, which produces an excitation radio-frequency field B1, and with a receiver coil 25. The volume coil is often termed a volume resonator in the literature. The receiver coil 25 is advantageously implemented as a surface coil. The transmitter coil 24 is normally at room temperature but could also be cooled.

The cryogenic receiver device 29 contains the receiver coil 25 with the associated electrical circuit 28 which, in turn, comprises a tune/match/detune circuit 26 and an advantageously also cooled preamplifier 27. A "tune/match" circuit is understood to be a circuit that adapts the impedance of the receiver coil to the preamplifier at the working frequency (NMR resonance frequency). This is necessary to achieve an optimum signal-to-noise ratio and is also general practice. The tuning and matching functions of the circuit are often treated separately. The "detune" circuit will be described in detail below.

Cooling of the cryogenic receiver device 29 can be achieved in various ways, e.g. by means of a closed cryogenic circuit using a cooler 30 or by immersing the receiver coil 25 and at least parts of the electrical circuit 28 in liquid nitrogen. The cooled receiver coil 25 is disposed in the immediate vicinity of the sample 31, which is usually at room temperature. In the example shown, the transmitter coil 24 is controlled by the transmitter TX to produce the excitation field B1. The signal from the preamplifier 27 is routed to the receiver RX, which finally digitizes the signals. The transmitter TX and receiver RX are connected to the MRI electronics 32, which contains the remaining components for operation.

In the above example, only one receiver coil 25 is depicted. In modern MRI systems, usually not one but multiple receiver coils operated in parallel are deployed ("receive-only coil arrays") [1], [2]. Each of these is then connected to its associated electrical circuit (28) and a corresponding receiver RX connected downstream. The signals of multiple receiver coils can also first be combined and then routed together to a receiver.

Configurations are also conceivable (and common practice in high-resolution NMR) in which one or more of the receiver coils are also used for transmission. For this purpose, an electronic switchover element (TX/RX switch) is connected at a suitable location between the receiver coil 25 and the preamplifier 27, which can switch the receiver coil to transmit TX for transmission. Such configurations can be used in the form of TX/RX single coils, TX/RX arrays and also combinations of TX/RX coils for different frequencies (nuclei) in MRI and also in NMR (not shown). In such configurations, the switchover element should advantageously also be operated in magnetic field $B_0$ inside the room temperature bore 23 to keep the losses upstream of the preamplifier at a minimum.

The objective of such configurations with a cryogenically cooled receiver system is to achieve the largest possible signal-to-noise ratio but with the smallest possible adverse impact on or limitation of other characteristics of the system. Here is a list of the most important points that the application must comply with:

1. To minimize the noise of the receiver coil itself, it is cooled and made of highly electrically conductive metals or superconducting materials.

2. It must additionally be ensured that the additional noise of the electrical circuit 28 connected downstream is minimized.

3. In the case of MRI systems, there is a further requirement: The receiver coil must be sufficiently decoupled from the transmitter coil because the transmission B1 of the transmitter coil and therefore the excitation in the region of the sample must not be influenced by the presence of the receiver coil (which, during reception, is tuned to the same NMR resonance frequency as the transmitter coil), to avoid artifacts due to inhomogeneous excitation. Nor must the interaction of the receiver coil with the B1 field of the transmitter coil result in damage or destruction of the receiver coil itself or other components. According to prior art, decoupling can be achieved by deactivating the receiver coil during transmission.

This deactivation is necessary for a geometry that optimizes the measurement results in a general configuration and with any orientation of the receiver coils (with respect to the sample and therefore also with respect to the transmitter coil), both in the case of single coils and, in particular, in the case of arrays. Only in the case of an individual receiver coil or receiver coil configurations in which the enclosed surfaces of all receiver coils are oriented exactly parallel to the B1 magnetic field of the transmitter coil can such a interaction be minimized ("geometric decoupling") because the magnetic flux resulting from B1 in the receiver coil is then zero and no voltage is therefore induced, and therefore no induced current can flow in the receiver coil(s). In a somewhat more general configuration of multiple receiver coils, however, there are always receiver coils that couple with the B1 field of the transmitter coil. In modern devices, in particular, so-called quadrature transmitter coils are used. (The coils produce a B1 rotating field wherein the B1 vector rotates with the NMR frequency about the axis that is provided by the $B_0$ field. This corresponds to a 90 degree phase-shifted overlap of two B1 field components that are linearly polarized and are perpendicular to the $B_0$ magnetic field). This rotating field (or at least one of the linear B1 components) then generally couples to each receiver coil. In this case, it is no longer possible to geometrically decouple all receiver coils from the transmitter coil.

4. The cryogenic receiver device must not produce any further artifacts either, e.g. in the form of $B_0$ field disturbances in the vicinity of the sample, caused by magnetizable materials, in particular, by the receiver coils themselves or by the electronic components of the electrical circuit. By magnetizable materials, those are meant here that exhibit a high magnetic susceptibility above $10^{-3}$ volume susceptibility MKS, in particular, ferromagnetic materials, such as iron, nickel, and cobalt.

The most important aspects to be achieved in a specific implementation are stated below:

1. In the approach considered here with cooled receiver coils in which the thermal noise is reduced and RF resistance may also be reduced, depending on the technology, it is advantageous if the downstream electrical circuit is also cryogenically cooled to minimize additional noise. In particular, in the case of cryogenic receiver coils, the preamplifier should also be cooled. It is then advantageous if the preamplifier is as close as possible to the receiver coil to minimize losses in the cables.

2. The cooling system must be able to keep all cooled components (receiver coil, cables, electrical circuit) at the intended temperature and to do this without causing any disturbances or other instabilities.

3. The materials and components used must not be magnetizable and must not cause disturbances of the static $B_0$ magnetic field in the sample, which can result in severe measurement artifacts or even signal cancellation.

4. To ensure the decoupling of the receiver coil from the transmitter coil discussed above, an additional functionality is required to deactivate the receiver coil during transmission. (In practice, this is achieved by effective opening/interruption of the coil circuit so that no induced current flows through the receiver coil [1]. This operation is often termed "detuning" in the literature.) Additional electronics are required to deactivate the receiver coils in this way. These should now be very close to the receiver coil to minimize RF losses and the associated additional noise because this circuit is, in a sense, part of the receiver coil, since the entire resonant coil current flows through this circuit as well as through the associated connecting cables to the receiver coil during reception.

5. The requirements stated above necessitate large-signal-resistant cooled electronics in the immediate vicinity of the coil and therefore in the magnetic field (in order to withstand the generally high power of the transmitter coil, which is in the kW range).

In cryogenically cooled NMR/MRI systems, there is a general requirement that semiconductors in a strong magnetic field should be operated at low temperatures and with good cooling, and the components must not be magnetizable. These semiconductor components are, for example, RF switching (PIN), RF limiters and varactor diodes, or active elements, such as field effect transistors. All these can be realized in different semiconductor technologies.

The simplest case is shown in FIG. 3. It is a planar structured diode with the negatively and positively doped regions (n, p). When an electrical potential is applied between anode 40 and cathode 41, the electrons (e−) move from the cathode toward the anode. If the polarity of the applied potential is reversed, the junction (w) builds up and current ceases to flow.

FIG. 4 shows a junction field effect transistor (FET) with a finger structure with the semiconductor material (N). The flow 45 of charge carriers (e+) from the drain 42 to the source 44 is controlled by the electric potential at the gate 43.

Attempting to operate the semiconductors under the necessary constraints stated above results in a number of problems.

1. Deflection in the magnetic field: The problem arises that moving charge carriers are deflected in the magnetic field, depending on their direction of movement. This results in distortion of the characteristic (gain, forward voltage, etc.) of the semiconductors, possibly even rendering them useless. Different directions of the B-field are possible.

In the example in FIG. 4, the E-field is oriented in the x-direction by the voltage applied between drain 42 and source 44. The electrical field exerts a force in the x-direction on the charge carriers (e+) with charge q (shown as holes in FIG. 4), which results in a current in the x-direction, depending on the mobility ($\mu$) [3] of the semiconductor. When a B-field is applied, an additional Lorentz force ($F=q \cdot v \times B$) is exerted, where v is the velocity of the charge carriers (F, v, and B are vectors in this case; the "×" sign is the cross product). The force may now be different depending on the orientation of B.

a) If B is only in the x-direction, no further effect occurs because the cross product is v×B=0.

b) If B is in the z-direction, the Lorentz force acts in the xy-plane.

FIG. 5 shows the xy-plane. The figure shows the movement of a charge carrier without collision with an E-field applied in the x-direction of −1V/μm and a B-field in the z-direction of −10T. For the mass of the charge carrier, a hole in GaAs with the effective mass $0.45 \cdot m_e$ was assumed ($m_e$ designates the electron mass). The charge carrier is at the origin and at rest at time zero. The general solution for movement of a charge carrier in a homogeneous E and B-field is provided by a cyclotron movement with a superposed drift movement, which results from the direction E×B. Under the given initial conditions, the particle initially moves in the x-direction. With increasing velocity, the Lorentz force increasingly also takes effect and deflects the particle in a curved path and the particle returns to the zero point of the x-axis, where it reverses its direction and the movement starts identically from the beginning again. With an increased magnetic field, the curvature of the path is more pronounced and the pattern is then scaled down in both spatial dimensions x and y.

However, this movement now only applies until the first collision. Without a collision, the global movement is in the y-direction only and no current flows from the drain to the source provided that the distance from the drain to the source is not below a certain value (in FIG. 5, this would be approx. 50 nm. However, because the movement is normally slowed down by collisions in a semiconductor, the charge carrier can only move a certain distance away from the origin without disturbance. After a collision, the procedure always starts again from the beginning under the same initial conditions. This results in an average movement that can be between the x-direction (frequent collisions or weak magnetic field) and the y-direction (few collisions or strong magnetic field), depending on the frequency of the collisions and the strength of the magnetic field. Another way of expressing the frequency of the collisions is the mobility (μ), which is calculated as: $\mu = q \cdot T_c / m_e$, where $T_c$ is the mean free time until the next collision and $m_e$ is the effective charge carrier mass.

The angle of the deviation of the mean direction of movement from the E-field direction is now shown in FIG. 6 as a function of the magnetic field for different mobilities μ, where, for the sake of illustration, $T_c$ is included in the calculation as a constant, rather than statistically distributed.

As long as the angle is small (e.g. smaller than 20 degrees), the path does not change significantly and neither do the properties of the semiconductor. As the angle increases, the distance to be covered increases until the extreme case of 90 degrees, at which it becomes infinite. This results in greater and greater resistance between the drain and the source. With a typical mobility of $\mu = 1$ m²/(Vs), which applies to GaAs (gallium arsenide) at 300K and a field strength of 1 T, the charge carriers are deflected on average by approximately 20 degrees with respect to the E-field direction. At lower temperatures, the mobility of GaAs is much greater (e.g. $\mu = 5$ m²/(Vs) at 77K). Further data are provided for silicon in [4]. The deflection is already almost 80 degrees in this case, at which point nearly no charge carriers arrive at the source from the drain and the semiconductor is no longer functional. The above consideration applies to semiconductor geometries that are considerably larger in the y-direction than in the z-direction, which is usually also the case for modern field effect transistors.

c) If B is in the y-direction, a force acts on the charge carriers in the z-direction. This deflects the charge carriers in the z-direction in addition to their normal movement in the x-direction. Because the thickness (z-direction) of the field effect transistor is very small, the drift movement of the charge carrier at the boundary of the conductive region is stopped and an electric opposing field (Hall field, [4]) builds up that is superimposed on the E-field in the z-direction (caused by the gate-source voltage) and therefore results in changes in the device characteristics. Because of the complex geometry, this effect cannot be precisely quantified.

The disadvantageous effects described in b) and c), typically occur with magnetic field strengths $B_0$ of 1 T or above wherein, depending the general conditions, the inventive measures become more and more necessary with fields of 1.5 T, 3 T or above. At very high field strengths of 7 T or more, they are practically indispensable.

2. Freezing: Additionally, at low temperatures, charge carriers increasingly freeze out and their concentration reduces, which also results in an increase in the electrical resistance. The two effects 1 and 2 reinforce each other and can have the following effects: In the case of a field effect transistor, the conductivity of the channel can be practically reduced to zero, making the element no longer usable. In the case of a diode, the conductivity is also reduced and the forward voltage increases for a given current such that, in an extreme case, the diode becomes practically completely insulating.

3. Dissipation: Depending on the application, dissipation occurs in the electronic components, which strongly heats the components if the power cannot be removed. This can completely prevent cooling in cryogenic operation or, in pulsed mode, heat the component in a pulsed manner. For example, a FET is to be cooled to reduce its background noise. Due to the quiescent current at the working point, so much power can already be dissipated that the FET cannot be sufficiently cooled and the noise is therefore excessively large.

4. Cooling: Semiconductor components with high power densities must be sufficiently cooled, which is often achieved with liquid nitrogen. This has the advantage that thermal power can be dissipated locally to a certain extent even without further design measures. However, as an unwanted side-effect, boiling with bubbling occurs above a certain power density. In the immediate vicinity of all electrical components, this results in modulation of the signal due to the variation of the density and therefore of the dielectric constant. This often results in very strongly stochastic phase modulations, which cause artifacts in the measurement data.

There are only a few published articles in prior art. Most cryogenically cooled reception systems can be classified in the following three categories (TX means transmit, RX means receive);

a) TX/RX with the same coil for both functions. This configuration does not require any electronics in the vicinity of the coil and many variants thereof are published in the literature.

For NMR applications, a configuration was published in [5]. This contains a cooled volume coil for transmission and reception. The associated electrical circuit is located outside the magnet.

[6] discloses a configuration for MRI with an HTS surface coil, which is cooled in LN2 and is operated in an RX/TX mode.

[7] discloses a further refined variation, which produces a quasi-homogeneous volume field with a Helmholtz configuration. This configuration is also operated in RX/TX mode. Neither of the two configurations have any cooled electronics.

b) RX-only (receive only) through a receiver coil wherein, in this case, this is geometrically decoupled from the transmitter coil (volume coil or resonator) (as shown in FIG. 2, but with B1 parallel to the coil surface of the receiver coil).

Such a configuration would as such also not require any electronics in the immediate vicinity of the receiver coil. However, because, in practice, the coupling between the transmitter coil and the receiver coil cannot be reduced sufficiently, the remaining coupling requires further measures. A very simple rudimentary configuration of this type was described in [8]. The function of the cooled electronics is limited to a purely passive reduction of the coupling of the receiver coil as compared with the transmitter coil, which is performed by two crossed diodes. However, this only works sufficiently with high power (hard pulses); at lower power, as is often used in NMR and MRI ('shaped pulse'), the diodes no longer have an effect. In this configuration, the diodes are apparently directly cooled in the liquid N2 bath. The remaining electronics are not cooled.

A further developed configuration was published in [9]. This contains a much more extensive electrical circuit. Results with this cryogenic configuration have been published that impose only moderate requirements on the electrical circuit if appropriately oriented with respect to the transmitter coil. The preamplifier is also not cooled in this configuration.

In [10], a planar array configuration in liquid N2 was published. This planar configuration, which permits geometric decoupling from the transmitter coil, only imposes moderate requirements on the electrical circuit. However, it does strongly limit the range of applications. Nothing is disclosed about the orientation of the electronic components.

c) A configuration with arbitrary orientation of the receiver coil with respect to the transmitter coil was published in [11]. An electrical circuit, which can be cooled, is located in the immediate vicinity of the coil and therefore in the magnetic field. It is not apparent whether and how the electronic components (junctions of the semiconductors) are oriented. The preamplifier is not part of the cooled configuration. This results in a loss of sensitivity. This configuration is prepared for cryogenic operation. The published measurements with the two-element array, in which for deactivation an electrical circuit is required in the immediate vicinity of the coil were, however, recorded at room temperature. Moreover, the intended cooling with liquid nitrogen would result in the signal modulations described above and therefore in artifacts in the measurements.

In summary, the literature does contain some initial possible devices but their function has only been demonstrated with restrictions. In particular, there are no devices in a general configuration of the receiver coils that can be used for receiver arrays. There has apparently been no success so far in implementing the electronics that are necessary for a general configuration of the coils and which meet all the requirements.

Such known configurations are sketched in FIGS. 7 and 8. The printed circuit board 70, 70' is directly placed in the liquid nitrogen 73 or is mounted on a heat sink 74 which is, in turn, in the liquid nitrogen. The semiconductor components 72, 72' are in a standard plastic housing 71, 71'. The perpendicular orientation of the semiconductor junction with respect to the magnetic field $B_0$ is often not controllable in such a design. The obvious solution, building the circuit with commercial components, often fails because of the ferromagnetic (Kovar) material used for the housing. The heat dissipation in commercial components is not optimal either because the housing would normally be mounted on a heat sink. However, this results in a conflict with the RF signal, which often has to be conveyed in an electrically insulated manner.

1. Housing made of plastic

This is completely useless for heat transmission at low temperatures. Transmission is only performed via the metal connector pins which, however, generally have an electrical potential and can therefore not be directly mounted on the metal heat sink. The thermal conductivity of plastics is very low at low temperatures and therefore unsuitable [12].

2. Housing made of ceramics and metal

In housings made of ceramics, better thermal connection is usually possible. However, the ceramic housings often have components made of Kovar, which results in uncontrollable field distortions and can even concentrate the magnetic field in the immediate vicinity of the semiconductor. In metal housings, nickel layers are often present that also result in field distortions and are therefore completely unwanted in the magnetic field.

All housings with magnetizable materials in the immediate vicinity of the measuring region additionally distort the $B_0$ field in the measurement volume and, as already mentioned, can result in artifacts in the measurement results.

The objective of this invention is to ensure undistorted characteristics of the semiconductor components used, in an electrical circuit of the type defined above, by the simplest possible technical means, despite the very strong magnetic field and the low operating temperatures.

SUMMARY OF THE INVENTION

This objective is achieved in a way that is surprisingly simple and effective with an electrical circuit of the type stated above, characterized in that at least one semiconductor junction of at least one of the semiconductor components of the electrical circuit is disposed such that the average direction of motion of the charge carriers in the semiconductor junction is essentially parallel to the lines of force of the magnetic field $B_0$, wherein the corresponding semiconductor component is disposed directly on a substrate, which is made of a material with good thermal conduction properties.

Despite all the problems of implementation, the real solution is to dispense with all housings of the semiconductor components (pins, incoming leads, etc.) and to mount the semiconductor chips directly on a substrate with good thermal conduction properties.

Here, "direct" can also mean a thin layer of glue or solder because these have no significant influence on the thermal and electrical properties. By "essentially parallel," a deviation of no more than 45 degrees is meant. By "good thermal conduction properties," more than 10 $Wm^{-1}K^{-1}$, preferably more than 100 $Wm^{-1}K^{-1}$ is meant.

For most applications, there is a requirement that the substrate material consists of an electrical insulator. The substrate used must be different from the substrates commonly used in electronics, such as FR4, Teflon etc. The materials used must exhibit a maximum thermal conductivity [12] at cryogenic temperatures. This is ensured with a substrate material consisting of ceramic aluminum oxide, aluminum nitride, sapphire, beryllium oxide, and/or silicon oxide. Other suitable materials can also be used. The optimum solution in practice for the desired cryogenic use is sapphire, which is completely unusual in electronics. This makes it necessary to solve the following technical problems:

Mounting and thermal connection of the semiconductors on a sapphire substrate is a technological challenge. It can be achieved by soldering, gluing (thermally conductive grease) etc., but must withstand the extreme temperature cycles during cooling and heating.

Electrical connection to the semiconductor components is also a problem. This can typically be achieved by bonding with aluminum or gold wire.

The overall configuration must be oriented in such a way that the condition that the orientation of the $B_0$ lines of force must be parallel to the direction of motion of the charge carriers is met.

FIG. 1 shows a specific example of such a configuration, this being the simplest case of a minimum cryogenic two-port.

For faultless operation, it is highly advantageous if no phase transition can occur in the medium 17 surrounding the device while it is in the operative state. Such a phase transition would, for example, occur with cooling in liquid nitrogen. The device is advantageously constituted so that it is in a vacuum. In this way, any modulations due to density fluctuations of a cooling medium are avoided. However, this assumes that the entire thermal conduction is performed exclusively via a solid body. For this purpose, a sapphire substrate is optimally used as the substrate 12.

Moreover, the substrate is connected to a heat sink. The heat sink is the cooling element 14, which is cooled by a cooling medium 15. The connection is represented here with a screw fastening 13 and thermally conductive grease between the substrate 12 and heat sink 14. The sapphire substrate is metallized with an appropriate conductor structure 18. The semiconductor component 10 is soldered onto the pad or glued and electrically contacted by means of a bond connection 11. The terminals 16 to the remaining circuit elements of the overall circuit, which are not critical in respect of the above requirements, can be connected via solder pads.

The configuration is oriented such that the requirement for orientation of the junction in the semiconductor component 10 with respect to the magnetic field $B_0$ is met.

This configuration is only representative of the basic principle. Of course, much more complex circuits are possible in this way. For circuits with multiple semiconductor elements, it is advantageous if all semiconductor junctions are oriented such that the direction of motion of the charge carriers is essentially parallel to the magnetic field lines.

The substrate can be electrically conductive in certain cases (semiconductor component has all terminals accessible at the top, which are contacted with two or more bond wires, or also terminals with which the chip is contacted directly to ground, e.g. in the case of limiter diodes). In the case of metals, good thermal conductivity is also provided. This enables the components to be disposed in such a way that the semiconductors can be thermally conductively connected to a substrate that consists of an electrically conductive substrate material. The substrate material can typically consist of copper, silver, or aluminum. The solution outlined here ensures that all materials used are non-magnetizable.

The details described can also be implemented differently. Depending on the application, RF switching, RF limiter, and/or varactor diodes can be used as semiconductor circuit element components. The electronic components can be implemented in different technologies. For the semiconductor components, the initial materials GaAs, GaN, silicon, germanium, SiGe can be used.

The scope of the invention also includes various methods for operating an electrical circuit of the type described above. The circuits implemented in this way can be used for varied purposes, such as:
- the electrical circuit is used to amplify a signal, wherein active elements, such as FET and or bipolar transistors, are used as semiconductor components;
- the electrical circuit is used for tuning a receiver coil;
- the electrical circuit is used for matching a receiver coil;
- the electrical circuit is used to reduce the current induced by the transmitter resonator in the receiver coil;
- the electrical circuit is used to switch over the receiver coil to transmit during transmission.

The inventive solution described above opens up new possibilities for implementing systems with much better performance for NMR and MRI receive devices. Of course, further variations that are not described can be implemented by a person skilled in the art.

Further advantages result from the description and the drawing. Moreover, the features stated above and further below can be used separately or together in any combination. The embodiments shown and described are not intended to be an exhaustive list, rather are examples to explain the invention.

The invention is shown in the drawing and is explained in more detail using the example of the embodiments. The figures show:

DESCRIPTION OF THE PREFERRED EMBODIMENT

Figure 1:
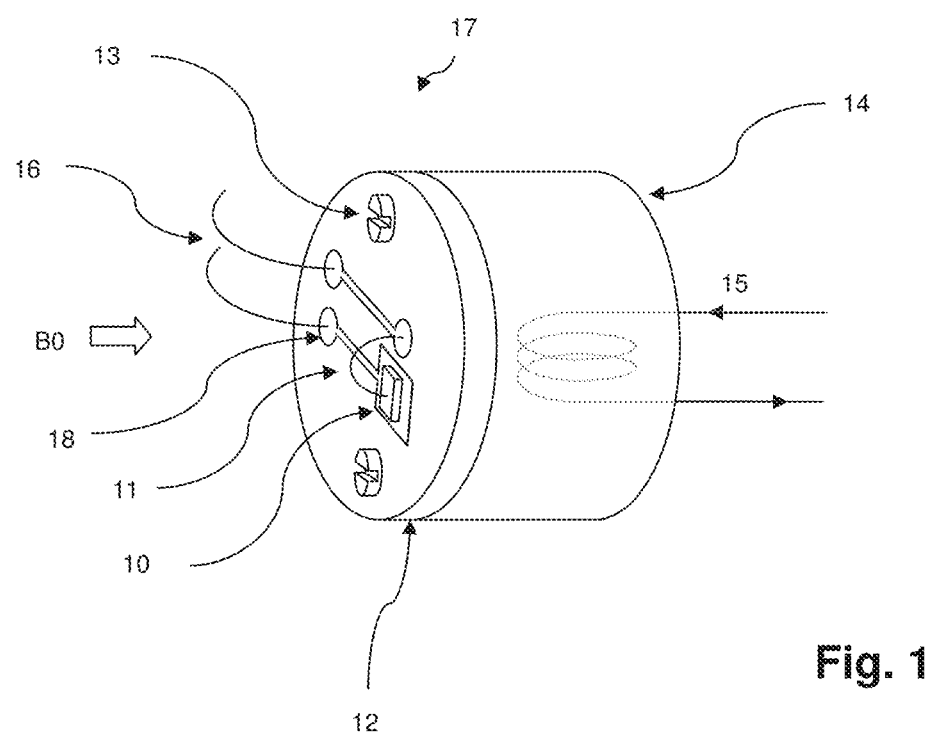
FIG. 1 an embodiment of the inventive device.
Figure 2:
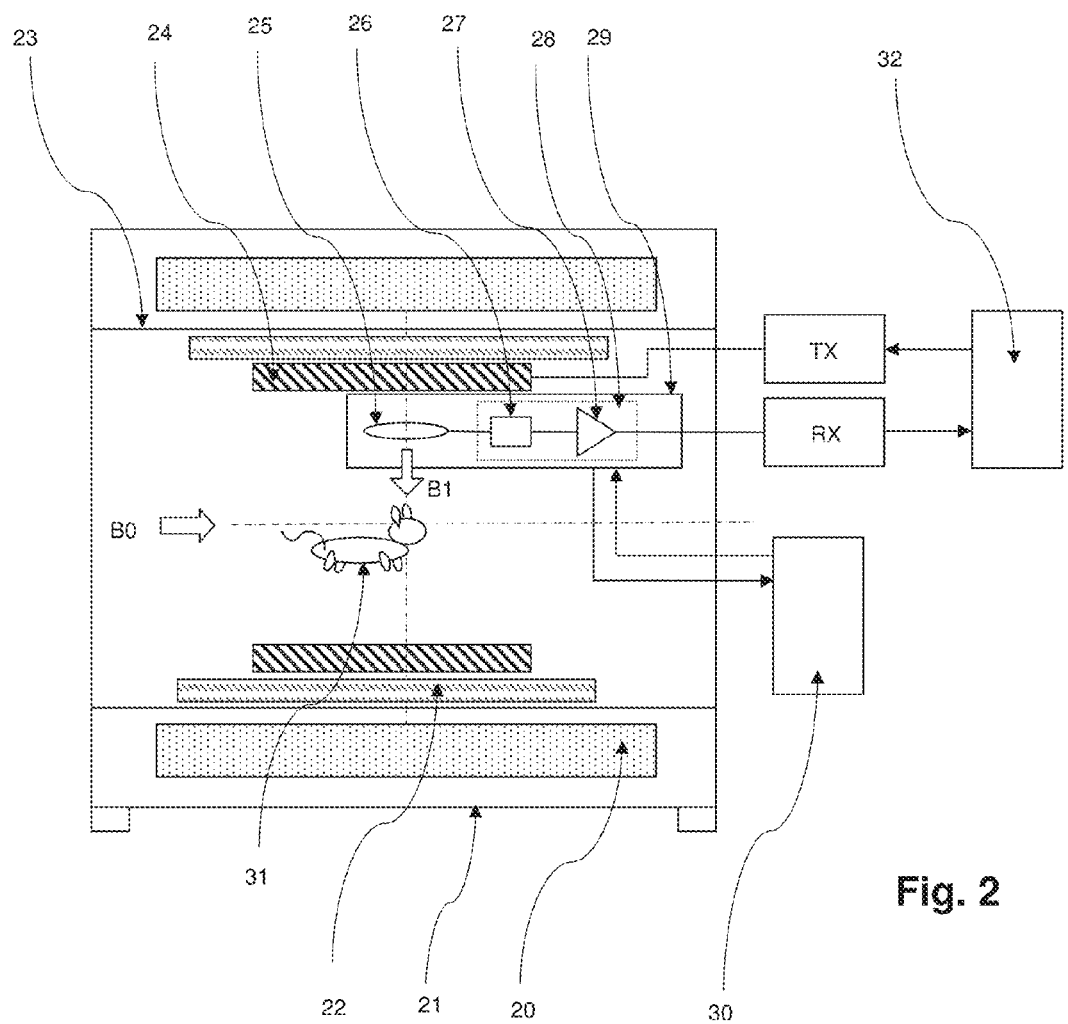
FIG. 2 a schematic overview of an MRI system.
Figure 3:
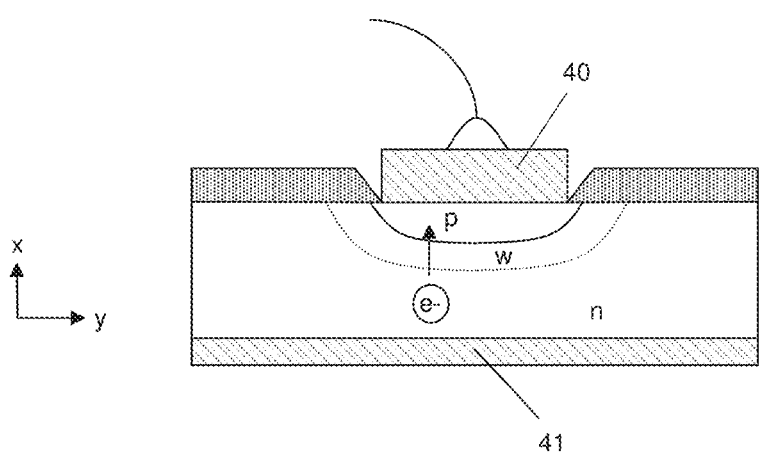
FIG. 3 the cross section of a planar structured diode.
Figure 4:
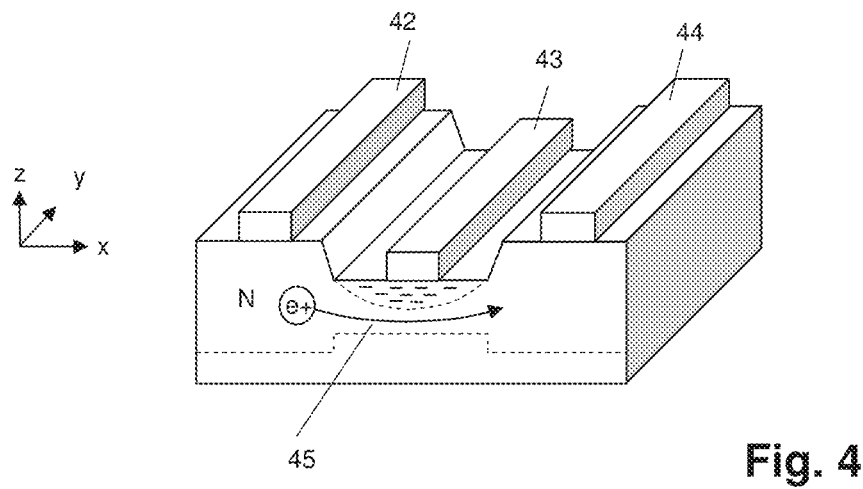
FIG. 4 a FET structure with a finger structure in an oblique view.
Figure 5:
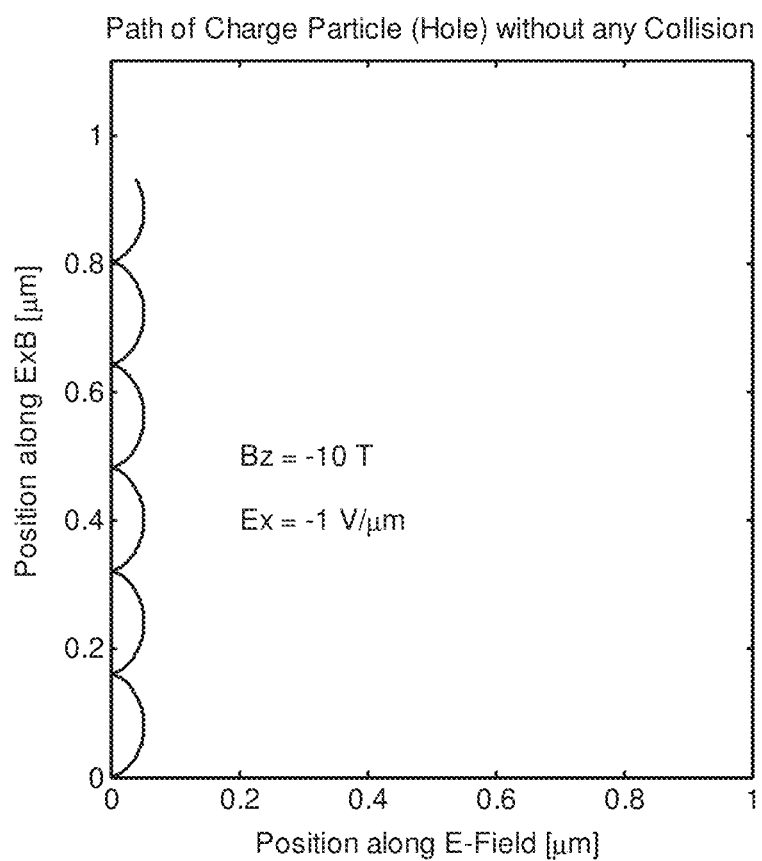
FIG. 5 the motion of a charge carrier in the xy-plane under the influence of an E and B-field.
Figure 6:
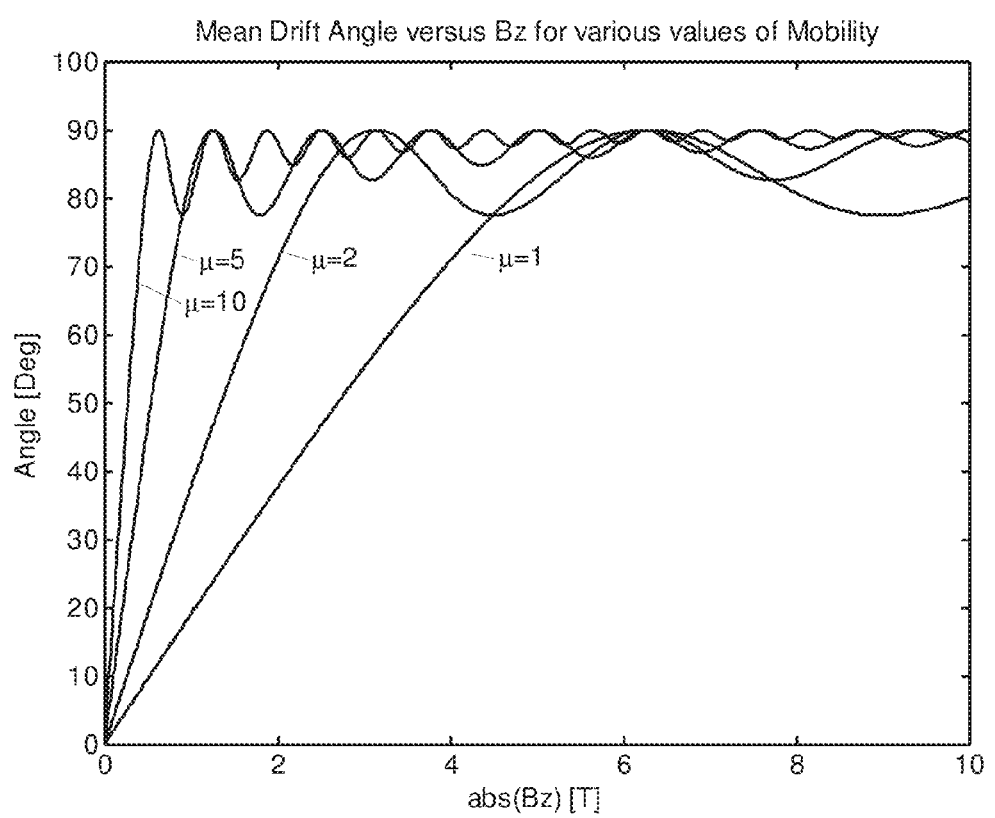
FIG. 6 the average drift angle of a charge carrier.
Figure 7:
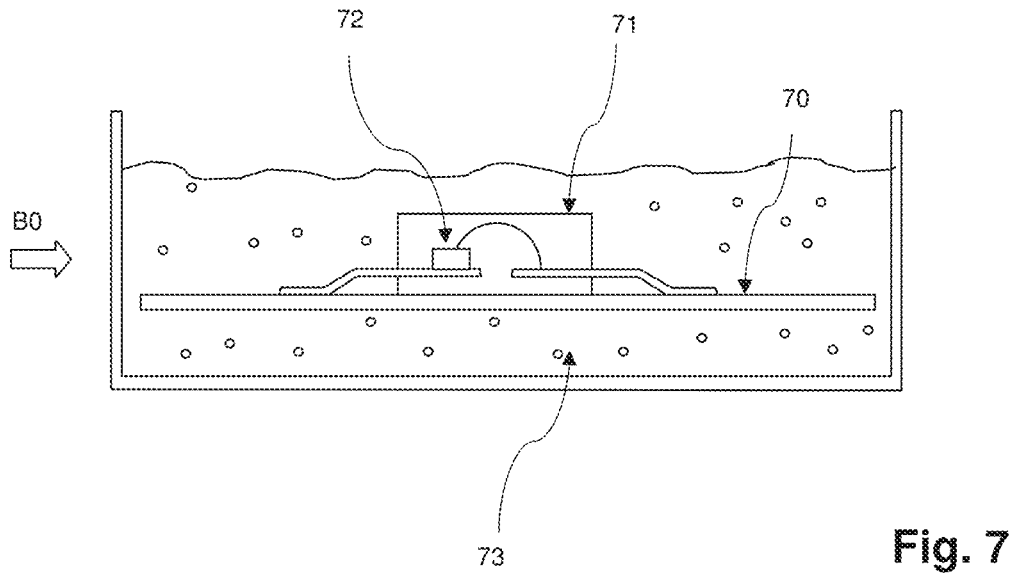
FIG. 7 prior art 1.
Figure 8:
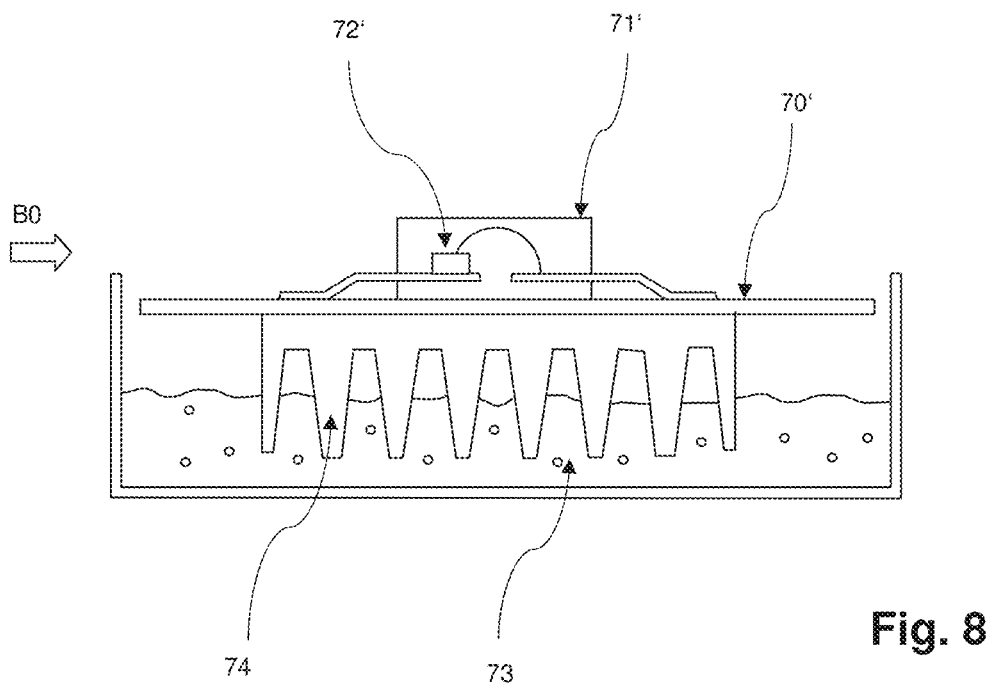
FIG. 8 prior art 2.

FIG. 1 illustrates an embodiment of the inventive electrical circuit with one or more semiconductor components 10 for use in an apparatus for MR (="magnetic resonance") spectroscopy or tomography with a preferably superconducting magnet 20 for producing a magnetic field in the direction of a z-axis in a working volume disposed on the z-axis about z=0, wherein the electrical circuit, as part of a cryogenic MR receive 29 and/or MR transmit device 24, is disposed at an operating temperature below 100K and in a magnetic field $B_0$ of at least 1T in the MR apparatus, which is characterized in that at least one semiconductor junction of at least one semiconductor component 10 of the electrical circuit is disposed such that the average direction of motion of the charge carriers in the semiconductor junction is essentially parallel to the lines of force of the magnetic field $B_0$, wherein the corresponding semiconductor component 10 is disposed directly on a substrate 12, which is made of a material with good thermal conduction properties.

| List of reference symbols | |
|---|---|
| Semiconductor component | 10 |
| Bond connection | 11 |
| Substrate | 12 |
| Screw fastening | 13 |
| Heat sink | 14 |
| Coolant | 15 |
| Terminals | 16 |
| Medium | 17 |
| Conductor structure | 18 |
| Magnetic field | $B_0$ |
| Magnet coil system | 20 |
| Dewar | 21 |
| Shim and gradient system | 22 |
| Room temperature bore | 23 |
| Transmitter coil | 24 |
| Receiver coil | 25 |
| Tune/match/detune circuit | 26 |
| Preamplifier | 27 |
| Electrical circuit | 28 |
| Cryogenic receiver device | 29 |
| Cooler | 30 |
| Sample | 31 |
| MRI electronics | 32 |
| Excitation field | $B_1$ |
| Transmitter | TX |
| Receiver | RX |
| Anode | 40 |

-continued

| List of reference symbols | |
|---|---|
| Cathode | 41 |
| Junction | w |
| Electron | e− |
| Positively doped region | p |
| Negatively doped region | n |
| Drain | 42 |
| Gate | 43 |
| Source | 44 |
| Charge carrier flow | 45 |
| Semiconductor material | N |
| Charge carrier | e+ |
| Printed circuit board | 70 |
| Plastic housing | 71 |
| Semiconductor component | 72 |
| Liquid nitrogen | 73 |
| Printed circuit board | 70' |
| Plastic housing | 71' |
| Semiconductor component | 72' |
| Liquid nitrogen | 73 |
| Heat sink | 74 |

LIST OF REFERENCES

[1] Roemer P B, Edelstein W A, Hayes C E, Souza S P, Mueller O M, The NMR Phased Array, Magnetic Resonance in Medicine 16 (1990), 192-225.
[2] Pruessmann K P, Weiger M, Scheidegger M B, Boesiger P, SENSE: Sensitivity Encoding for Fast MRI, Magnetic Resonance in Medicine 42 (1999), 952-962.
[3] http://de.wikipedia.org/wiki/Beweglichkeit_(Physik)
[4] Sze S M, Semiconductor Devices, Physics and Technology, J. Wiley & Sons (1985), ISBN 0-471-87424-8.
[5] Styles P, Soffe N F, Scott C A, Cragg D A, Row F, White D J, White P C J, A High-Resolution NMR Probe in Which the Coil and Preamplifier Are Cooled with Liquid Helium, Journal of Magnetic Resonance 60 (1984), 397-404.
[6] Black R D, Early T, Roemer P, Mueller O, Mogro-Campero A, Turner L, Johnson G, A high-temperature superconducting receiver for nuclear magnetic resonance microscopy, Science 259 (1993), 793-795.
[7] Nouls J C, Izenson M G, Greeley H P, Johnson G A, Design of a superconducting volume coil for magnetic resonance microscopy of the mouse brain, Journal of Magnetic Resonance 191 (2008), 231-238.
[8] Wright A C, Song H K, Wehrli F W, In Vivo MR Micro Imaging With Conventional Radiofrequency Coils Cooled to 77K. Magnetic Resonance in Medicine 43 (2000), 163-169.
[9] Wosik J, Bockhorst K H, I-Chih T, Narayana P A, Superconducting Receive-only 7 Tesla Coil for High Resolution Rat Brain DTI, Proc. Intl. Soc. Mag. Reson. Med. 20 (2012).
[10] U.S. Pat. No. 7,002,348 B2
[11] Wosik J, Nesteruk. K, Kamel M R, Ip F, Xue L, Wright A C, Wehrli F W, Cryogenic Varactor-Tuned 4-element Array and Cryostat for μ-MRI of Trabecular Bone in the Distal Tibia, Proc. Intl. Soc. Mag. Reson. Med. 16 (2008).
[12] Edited by Reed P R, Clark A F, Materials at Low Temperatures, National Bureau of Standards Boulder, Colo. American Society for Metals, ISBN: 0-87170-146-4

We claim:

1. An electrical circuit adapted for use in an MR apparatus, the MR apparatus structured for MR ("magnetic resonance") spectroscopy or tomography, the MR apparatus comprising:
a magnet or a superconducting magnet structured to produce a $B_0$ magnetic field of at least 1T in a direction of a z-axis in a working volume disposed on the z-axis about z=0;
a cryogenic MR receiver; and
an MR transmitter, wherein the electrical circuit is disposed in the MR apparatus as part of the cryogenic MR receiver and/or of the MR transmitter at an operating temperature below 100K and in the $B_0$ magnetic field, the electrical circuit comprising:
one or more semiconductor components, wherein at least one semiconductor junction of at least one of said semiconductor components is disposed such that an average direction of motion of charge carriers in said semiconductor junction is substantially parallel to lines of force of the $B_0$ magnetic field; and
a substrate, said substrate being made of a material having thermal conduction properties better than $10\,\mathrm{Wm^{-1}K^{-1}}$, wherein said semiconductor component having said semiconductor junction is directly disposed on said substrate.

2. The electrical circuit of claim 1, wherein all said semiconductor junctions of all said semiconductor components of the electrical circuit are oriented such that said direction of motion of said charge carriers is substantially parallel to the $B_0$ magnetic field lines of force.

3. The electrical circuit of claim 1, wherein said substrate is made of an electrically conductive substrate material and said semiconductor components of said electrical circuit are thermally conductively connected to said substrate.

4. The electrical circuit of claim 3, wherein said substrate material comprises copper, silver and/or aluminum.

5. The electrical circuit of claim 1, wherein said substrate is made of an electrically insulating material.

6. The electrical circuit of claim 5, wherein said substrate material comprises ceramic aluminum oxide, aluminum nitride, sapphire, beryllium oxide and/or silicon oxide.

7. The electrical circuit of claim 1, wherein the electrical circuit is disposed in a vacuum.

8. The electrical circuit of claim 1, wherein said substrate is made of a material having thermal conduction properties better than $10\,\mathrm{Wm^{-1}K^{-1}}$, which is connected to a heat sink.

9. The electrical circuit of claim 1, wherein all materials used are non-magnetizable.

10. The electrical circuit of claim 1, wherein RF ("radio frequency") switching diodes, RF limiter diodes and/or varactor diodes are provided as said semiconductor components.

11. The electrical circuit of claim 1, wherein active elements FET and/or bipolar transistors are provided as said semiconductor components.

12. The electrical circuit of claim 1, wherein initial materials of said semiconductor components comprise GaAs, GaN, silicon, germanium and/or SiGe.

13. A method for operating the electrical circuit of claim 1, the method comprising the step of amplifying an MR signal.

14. A method for operating the electrical circuit of claim 1, the method comprising the step of tuning and/or matching an MR receiver coil.

15. A method for operating the electrical circuit of claim 1, the method comprising the step of reducing a current induced by an MR transmitter coil in an MR receiver coil and/or switching over the MR receiver coil to transmit during transmission.

* * * * *